(12) United States Patent
Ishihara

(10) Patent No.: US 10,182,794 B2
(45) Date of Patent: Jan. 22, 2019

(54) ULTRASOUND DIAGNOSTIC APPARATUS AND ULTRASOUND IMAGE PRODUCING METHOD

(71) Applicant: FUJIFILM Corporation, Tokyo (JP)

(72) Inventor: Keitarou Ishihara, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 606 days.

(21) Appl. No.: 14/226,346

(22) Filed: Mar. 26, 2014

(65) Prior Publication Data

US 2014/0293739 A1 Oct. 2, 2014

(30) Foreign Application Priority Data

Mar. 26, 2013 (JP) ................................ 2013-064774

(51) Int. Cl.
*A61B 8/00* (2006.01)
*A61B 8/08* (2006.01)
(Continued)

(52) U.S. Cl.
CPC .......... *A61B 8/5207* (2013.01); *A61B 8/4494* (2013.01); *G01S 7/52028* (2013.01);
(Continued)

(58) Field of Classification Search
CPC ..... A61B 8/5207; A61B 8/4494; A61B 8/145; G01S 7/52028; G01S 15/8915; G10K 11/346
(Continued)

(56) References Cited

U.S. PATENT DOCUMENTS 6,325,759 B1 * 12/2001 Pelissier .................. A61B 8/06
600/443
2005/0113693 A1 * 5/2005 Smith ...................... A61B 8/12
600/439
(Continued)

FOREIGN PATENT DOCUMENTS

JP 2007-239 A 1/2007
JP 2007054191 A * 3/2007 ............... A61B 8/00

OTHER PUBLICATIONS

Machine Translation of JP 2007054191, 2007.*

*Primary Examiner* — James R Hulka
(74) *Attorney, Agent, or Firm* — Birch, Stewart, Kolasch & Birch, LLP

(57) ABSTRACT

An ultrasound diagnostic apparatus comprises a reception data memory that sequentially stores therein pieces of reception data; a beam forming unit that has a cache memory and that divides the pieces of reception data stored in the reception data memory into plural groups, sequentially transfers the plural groups to the cache memory, and performs stepwise phasing addition on the plural groups transferred to the cache memory; and a digital beam forming controller that obtains in advance a total amount of reception data to be used in the phasing addition according to the imaging condition, and controls the beam forming unit in accordance with the total amount of reception data and the cache memory capacity such that the beam forming unit divides the pieces of reception data into the plural groups so as to each fit into the cache memory capacity.

8 Claims, 2 Drawing Sheets

(51) Int. Cl.
*G01S 7/52* (2006.01)
*G01S 15/89* (2006.01)
*G10K 11/34* (2006.01)
*A61B 8/14* (2006.01)

(52) U.S. Cl.
CPC ........ *G01S 15/8915* (2013.01); *G10K 11/346* (2013.01); *A61B 8/145* (2013.01)

(58) Field of Classification Search
USPC .......................................................... 367/11
See application file for complete search history.

(56) References Cited

U.S. PATENT DOCUMENTS

| | | | | |
|---|---|---|---|---|
| 2005/0113694 | A1* | 5/2005 | Haugen | A61B 8/14 600/443 |
| 2005/0251037 | A1* | 11/2005 | Watanabe | A61B 8/08 600/437 |
| 2013/0116566 | A1* | 5/2013 | Sato | G01S 15/8961 600/447 |

* cited by examiner

ULTRASOUND DIAGNOSTIC APPARATUS AND ULTRASOUND IMAGE PRODUCING METHOD

BACKGROUND OF THE INVENTION

The present invention relates to an ultrasound diagnostic apparatus and an ultrasound image producing method and particularly to an ultrasound diagnostic apparatus that produces an ultrasound image by efficiently processing reception data acquired through transmission and reception of ultrasonic waves from a transducer array.

Background Art

Conventionally, ultrasound diagnostic apparatuses using ultrasound images are employed in medicine. In general, this type of ultrasound diagnostic apparatus comprises an ultrasound probe having a built-in transducer array and an apparatus body connected to the ultrasound probe. The ultrasound probe transmits ultrasonic waves toward a subject and receives ultrasonic echoes from the subject through each channel of the ultrasound probe, and the apparatus body electrically processes the reception signals to produce an ultrasound image.

In production of an ultrasound image, the apparatus body performs digital beam forming (DBF) processing by subjecting reception data acquired through each channel to phasing addition by a phasing adder. At that time, the amount of reception data used in the processing is extremely large and therefore the DBF processing is generally performed by a hardware to prevent the reception data from consuming the memory bandwidth and decreasing the processing speed. In recent years, however, there is a demand for performing the DBF processing by a software and how to smoothly process the reception data is now becoming an issue.

For instance, when pieces of reception data from sixty-four channels are subjected to phasing addition to form one sound ray, the pieces of reception data entered from all the channels and temporarily stored in a main memory are sequentially transferred to a cache memory of the phasing adder to be subjected to phasing addition. The cache memory here has a small capacity. Accordingly, if the pieces of reception data from sixty-four channels are subjected to phasing addition at a time, the calculation is performed with specific reception data from the same channel being repeatedly input and output to and from the cache memory (cache-out) and this causes frequent occurrence of cache-out, resulting in the decrease in the processing speed. Alternatively, dividing the pieces of reception data from sixty-four channels stored in a main memory into several groups and subjecting the same to phasing addition may be one possible measure. However, even if the reception data is randomly divided and transferred to a cache memory, a cache-out still frequently occurs and hence, the processing speed cannot be greatly improved.

To cope with it, for example, JP 2007-000239 A discloses an ultrasound diagnostic apparatus that transfers frame data with taking the cache function of an image forming section into account. In this ultrasound diagnostic apparatus, frame data is transferred from a main memory to a cache memory of the image forming section in block units which have been set for volume data in the main memory. Since the blocks of data are transferred in such an order that the possibility of subsequent use of the blocks of data transferred and temporarily stored in the cache memory is increased, the frequency of cache-out occurrence can be decreased.

SUMMARY OF THE INVENTION

In JP 2007-000239 A, however, the block unit which is used when the data is transferred from the main memory to the cache memory cannot be changed in accordance with imaging conditions. Accordingly, in the case of, the DBF processing in which the amount of reception data to be subjected to phasing addition greatly varies depending on imaging conditions, it is difficult to sequentially transfer the reception data by the right amount with respect to the capacity of the cache memory.

An object of the present invention is to solve the foregoing drawback in the prior art and to provide an ultrasound diagnostic apparatus and an ultrasound image producing method capable of sequentially transferring the right amounts of groups of reception data to be subjected to the beam forming processing from a main memory to a cache memory.

An ultrasound diagnostic apparatus according to the present invention comprises a transducer array having channels; a transmission driver adapted to transmit ultrasonic beams from the transducer array toward a subject according to an imaging condition; reception signal processors adapted to process reception signals outputted through the channels of the transducer array having received ultrasonic echoes from the subject; an image producer adapted to produce an ultrasound image from pieces of reception data acquired through the reception signal processors; a reception data memory adapted to sequentially store therein the pieces of reception data which have been produced from the reception signals received by the channels of the transducer array; a beam forming unit having a cache memory and adapted to divide the pieces of reception data stored in the reception data memory into a plurality of groups, sequentially transfer the plurality of groups of the pieces of reception data to the cache memory, and perform stepwise phasing addition on the plurality of groups of the pieces of reception data transferred to the cache memory; and a digital beam forming controller adapted to obtain in advance a total amount of reception data to be used in the phasing addition performed by the beam forming unit according to the imaging condition, and control the beam forming unit in accordance with the total amount of reception data and a capacity of the cache memory such that the beam forming unit divides the pieces of reception data in the reception data memory into the plurality of groups so as to each fit into the capacity of the cache memory and transfers the plurality of groups of the pieces of reception data.

The digital beam forming controller can obtain, as the total amount of reception data, an amount of reception data transmitted through the channels and used for producing one sound ray signal.

Preferably, the digital beam forming controller controls the beam forming unit so as to sequentially perform the phasing addition on the pieces of reception data transferred from the reception data memory to the cache memory.

Preferably, the digital beam forming controller divides the total amount of reception data into the plurality of groups that are substantially equal in size so as to each fit into the capacity of the cache memory, and causes the plurality of groups of reception data to be transferred to the cache memory.

The digital beam forming controller can divide the pieces of reception data into the plurality of groups in units of the channels and cause the plurality of groups of the pieces of reception data to be transferred to the cache memory such that the phasing addition performed by the beam forming unit is completed separately for each of the plurality of groups of the pieces of reception data. Alternatively, the digital beam forming controller can divide the pieces of reception data in a depth direction into the plurality of groups and cause the plurality of groups of the pieces of reception data to be transferred to the cache memory such that the phasing addition performed by the beam forming unit is completed separately for each of the plurality of groups of the pieces of reception data.

The imaging condition can be at least one of a frequency of ultrasonic waves, a scanning range and a scanning depth.

An ultrasound image producing method according to the present invention comprises the steps of: transmitting ultrasonic beams from a transducer array toward a subject according to an imaging condition; producing pieces of reception data by processing reception signals, by reception signal processors, outputted through channels of the transducer array having received ultrasonic echoes from the subject; sequentially storing in a reception data memory the pieces of reception data which have been produced by the reception signal processors from the reception signals received by the channels of the transducer array; dividing the pieces of reception data stored in the reception data memory and having time differences into a plurality of groups, sequentially transferring the plurality of groups of the pieces of reception data to a cache memory of a beam forming unit, and performing stepwise phasing addition by the beam forming unit on the plurality of groups of the pieces of reception data transferred to the cache memory; obtaining in advance a total amount of reception data to be used in phasing addition performed by the beam forming unit according to the imaging condition, and controlling the beam forming unit by a digital beam forming controller in accordance with the total amount of reception data and a capacity of the cache memory such that the beam forming unit divides the pieces of reception data in the reception data memory into the plurality of groups so as to each fit into the capacity of the cache memory and transfers the plurality of groups of the pieces of reception data to the cache memory; and producing an ultrasound image by an image producer from the pieces of reception data acquired through the beam forming unit.

According to the present invention, the total amount of reception data used in phasing addition is obtained in advance based on the imaging condition, and the reception data in the reception data memory is divided into a plurality of groups in accordance with the total amount of reception data and the capacity of the cache memory and then transferred to the cache memory to thereby suppress the frequency of cache-out. Therefore, the right amounts of groups of reception data to be subjected to the beam forming processing can be sequentially transferred from the main memory to the cache memory.

DETAILED DESCRIPTION OF THE INVENTION

An embodiment of the present invention will be described below based on the appended drawings.

Figure 1:
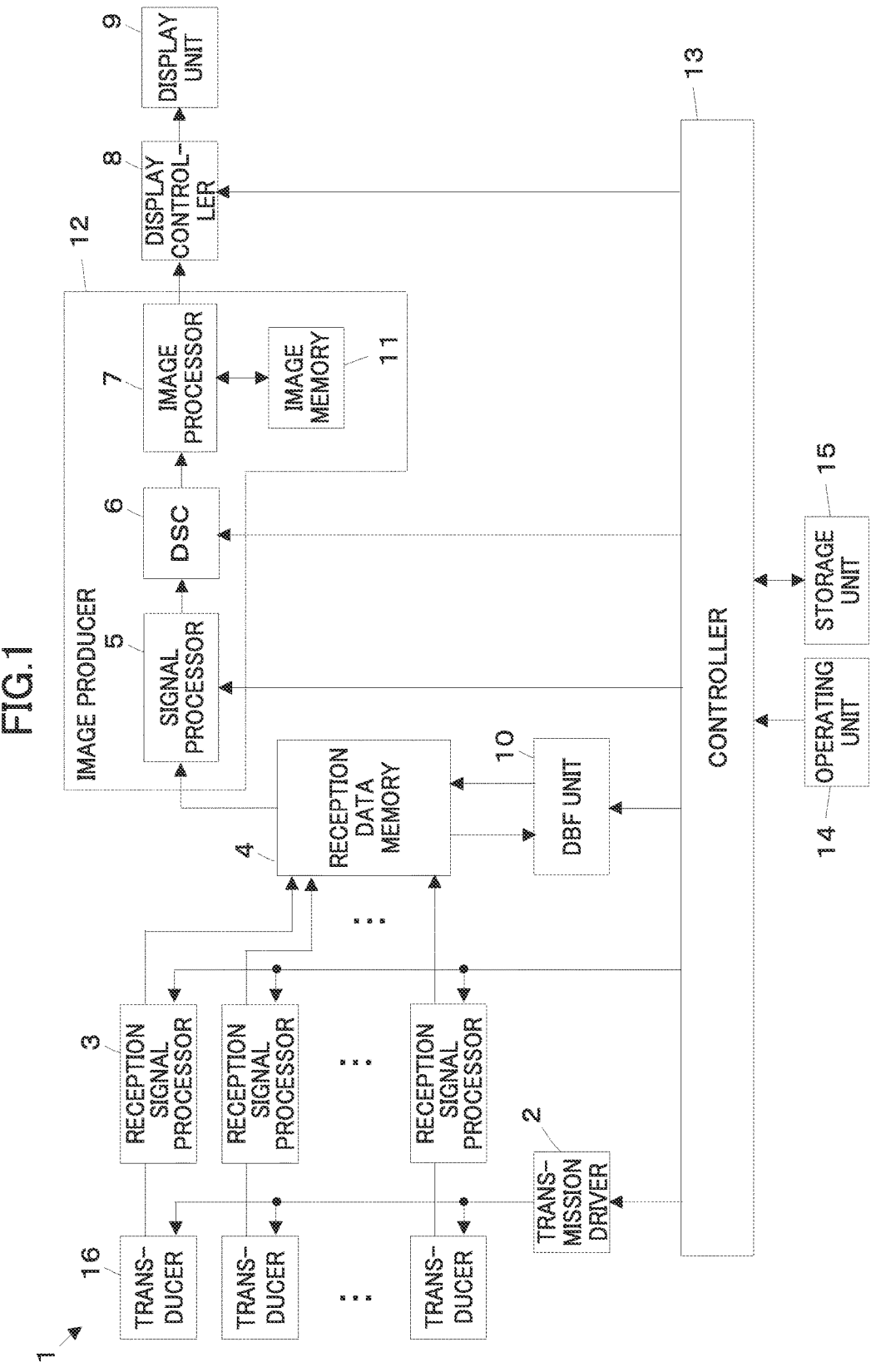
FIG. 1 is a block diagram showing the configuration of an ultrasound diagnostic apparatus according to an embodiment of the invention.

FIG. 1 shows the configuration of an ultrasound diagnostic apparatus according to an embodiment of the invention. The ultrasound diagnostic apparatus includes a transducer array 1, and a transmission driver 2 and a plurality of reception signal processors 3 are connected to the transducer array 1. A reception data memory 4 is connected to the reception signal processors 3, and a signal processor 5, a digital scan converter (DSC) 6, an image processor 7, a display controller 8 and a display unit 9 are connected serially to the reception data memory 4. A DBF unit 10 is connected to the reception data memory 4, whereas an image memory 11 is connected to the image processor 7. The signal processor 5, the DSC 6, the image processor 7 and the image memory 11 constitute an image producer 12.

A controller 13 is connected to the transmission driver 2, the reception signal processors 3, the DBF unit 10, the signal processor 5, the DSC 6 and the display controller 8, whereas an operating unit 14 and a storage unit 15 are connected to the controller 13.

The transducer array 1 includes a plurality of ultrasound transducers 16 making up a plurality of channels of a one-dimensional or two-dimensional array, and the transducers 16 are connected to the transmission driver 2. The transducers 16 are respectively connected to their corresponding reception signal processors 3. The transducers 16 each transmit ultrasonic waves according to driving signals supplied from the transmission driver 2 and receive ultrasonic echoes from the subject to output reception signals. Each of the transducer elements comprises a vibrator composed of a piezoelectric body and electrodes separately provided on both ends of the piezoelectric body. The piezoelectric body is composed of, for example, a piezoelectric ceramic typified by a lead zirconate titanate (PZT), a piezoelectric polymer typified by polyvinylidene fluoride (PVDF), or a piezoelectric monocrystal typified by lead magnesium niobate-lead titanate solid solution (PMN-PT).

When the electrodes of each of the vibrators are supplied with a pulsed voltage or a continuous-wave voltage, the piezoelectric body expands and contracts to cause the vibrator to produce pulsed or continuous ultrasonic waves. These ultrasonic waves are synthesized to form an ultrasonic beam. Upon reception of propagating ultrasonic waves, the vibrators each expand and contract to produce an electric signal and the electric signal is then output as a reception signal of the ultrasonic waves.

The transmission driver 2 including, for example, a plurality of pulsars adjusts delay amounts of driving signals based on a transmission delay pattern selected by the controller 13 so that the ultrasonic waves transmitted from the transducers 16 form an ultrasonic beam, and supplies the adjusted signals to the transducer array 1.

The reception signal processor 3 amplifies and A/D converts the reception signal output from the corresponding transducer 16 to produce reception data.

The reception data memory 4 is constituted in the main memory to sequentially store therein the reception data produced by the reception signal processors 3 frame by frame.

The DBF unit 10 constitutes a beam forming unit in the present invention and performs digital beam forming (DBF) by subjecting the reception data stored in the reception data memory 4 to phasing addition. By this digital beam forming, the ultrasonic echo is well focused so as to produce a base band signal (sound ray signal).

The signal processor 5 corrects the sound ray signals produced by the DBF unit 10 for the attenuation due to distance according to the depth at which the ultrasonic waves are reflected, and then performs an envelope detection process. By this process, the signal processor 5 produces a B-mode image data which is tomographic image information relating to the tissue in the subject.

The DSC 6 converts the B-mode image data produced by the signal processor 5 into image data compatible with an ordinary television signal scanning mode (raster conversion).

The image processor 7 performs required various processing including gradation processing on the B-mode image data entered from the DSC 6 and then outputs the B-mode image data to the display controller 8 and also to the image memory 11 so that the B-mode image data is stored therein.

The display controller 8 causes the display unit 9 to display an ultrasound diagnostic image based on the B-mode image data entered from the image processor 7.

The display unit 9 includes, for example, a display device such as an LCD and displays an ultrasound diagnostic image under the control of the display controller 8.

The operating unit 14 is provided for the operator to input information such as imaging conditions and may be composed of, for example, a keyboard, a mouse, a track ball, and/or a touch panel.

The storage unit 15 stores, for example, an operation program and may be constituted by, for example, a recording medium such as a hard disk, a flexible disk, an MO, an MT, a RAM, a CD-ROM, a DVD-ROM, an SD card, a CF card and a USB memory, or a server.

The controller 13 controls the components in the ultrasound diagnostic apparatus according to various instruction signals and the like entered by the operator through the operating unit 14.

The signal processor 5, the DSC 6, the image processor 7, the display controller 8 and the controller 13 are each constituted by a CPU and an operation program for causing the CPU to perform various kinds of processing but they may be each constituted by a digital circuit. The aforementioned operation program is stored in the storage unit 15. The recording medium in the storage unit 15 may be a flexible disk, an MO, an MT, a RAM, a CD-ROM, a DVD-ROM or the like in addition to a built-in hard disk.

Next, the DBF unit 10 and the controller 13 will be described in details.

Figure 2:
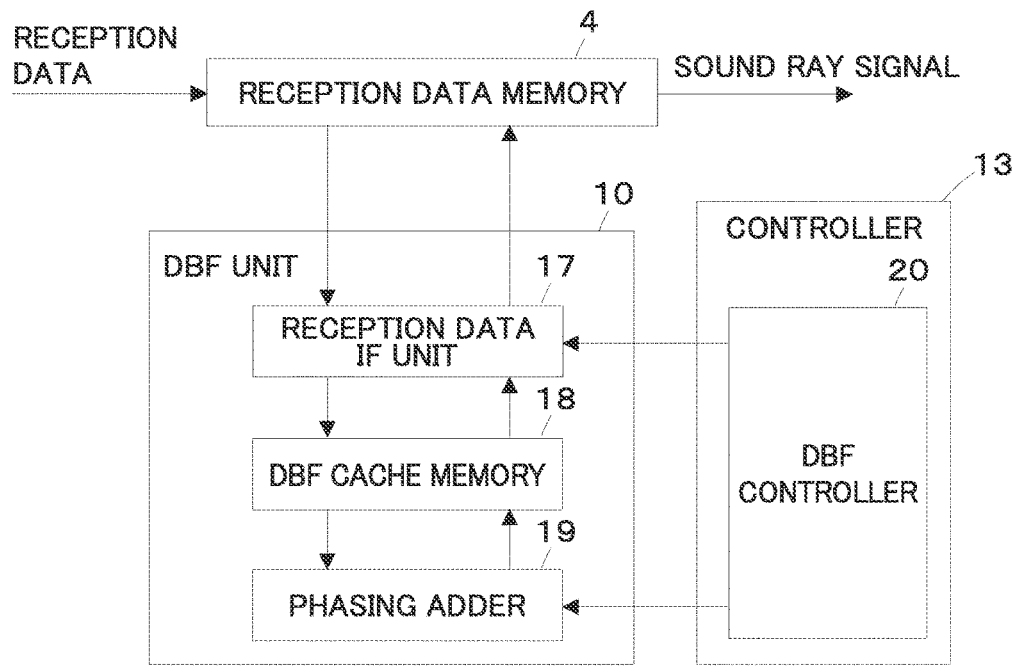
FIG. 2 is a block diagram showing the configuration of a DBF unit.

As shown in FIG. 2, the DBF unit 10 has a reception data interface (IF) unit 17 connected to the reception data memory 4, as well as a digital beam forming (DBF) cache memory 18 and a phasing adder 19 both connected in sequence to the reception data IF unit 17. The controller 13 includes a DBF controller 20, and the reception data IF unit 17 and the phasing adder 19 are connected to the DBF controller 20.

The reception data IF unit 17 serves as the intermediary of transfer of data between the reception data memory 4 and the DBF cache memory 18 under the control of the DBF controller 20. The DBF cache memory 18 temporarily stores the reception data transferred from the reception data memory 4 via the reception data IF unit 17 and temporarily stores sound ray data produced by the phasing adder 19. The phasing adder 19 performs phasing addition on the reception data stored in the DBF cache memory 18 under the control of the DBF controller 20.

The DBF controller 20 is configured to control the operation of the DBF unit 10 and to implement so-called software processing. Specifically, the DBF controller 20 previously calculates the total amount of reception data to be subjected to phasing addition performed by the DBF unit 10 based on the imaging conditions.

The total amount of reception data here refers to the amount of reception data necessary for producing at least one of sound ray signals used for producing an ultrasound image. The imaging conditions include factors to be considered in calculation of the total amount of reception data, such as the frequency of ultrasonic waves, a scanning range, a scanning depth (the number of times of sampling) and a type of the ultrasound probe.

Subsequently, the DBF controller 20 calculates the amount of reception data to be transferred from the reception data memory 4 to the DBF cache memory 18 based on the obtained total amount of reception data and the capacity of the DBF cache memory 18 so that the frequency of cache-out occurrence is suppressed, divides the reception data into a plurality of groups, and sequentially transfers the groups of reception data from the reception data memory 4 to the DBF cache memory 18 via the reception data IF unit 17.

For instance, the DBF controller 20 divides the total amount of reception data into substantially equal sized groups so as to each fit into the capacity of the DBF cache memory 18, thereby enabling to transfer the reception data to the DBF cache memory 18. At that time, it is preferred that the DBF controller 20 divide the reception data into a plurality of groups in units of channels and transfer the groups of reception data to the DBF cache memory 18 so that the phasing addition performed by the phasing adder 19 is completed separately for each group of reception data. This configuration can reduce the number of times the same reception data is input and output to and from the DBF cache memory 18 through the digital beam forming processing and accordingly, suppress the frequency of cache-out occurrence.

Furthermore, the DBF controller 20 controls the phasing adder 19 based on the amount of reception data divided into a plurality of groups and transferred from the reception data memory 4 to the DBF cache memory 18 so that the phasing adder 19 sequentially performs phasing addition separately on the respective groups of reception data transferred to the DBF cache memory 18.

Specifically, the DBF controller 20 selects a reception delay pattern from a plurality of previously stored reception delay patterns according to a reception direction that is set based on the imaging conditions. Then, based on the selected reception delay pattern, the phasing adder 19 provides corresponding delays to respective pieces of reception data, which have been produced based on the reception signals transmitted through the channels and have time differences, and adds them up under the control of the DBF controller 20. The digital beam forming is performed by subjecting each group of reception data stored in the cache memory 18 to phasing addition stepwise and by processing and integrating all the reception data from all the channels, thereby producing a baseband signal (sound ray signal) where the ultrasonic echo is well focused.

Every time one sound ray signal is produced for instance, the DBF controller 20 transfers the sound ray signal to the reception data memory 4 via the DBF cache memory 18 and the reception data IF unit 17.

Next, the operation of an embodiment will be described.

First, the operator inputs imaging conditions through the operating unit 14 of the ultrasound diagnostic apparatus. For example, the frequency of ultrasonic waves, a scanning range, a scanning depth, a type of the ultrasound probe and the like are input. The input imaging conditions are output to the controller 13 and the controller 13 controls each component of the ultrasound diagnostic apparatus to start the ultrasound diagnosis based on the imaging conditions.

Upon the start of the ultrasound diagnosis, driving signals are supplied from the transmission driver 2 under the control of the controller 13 so that the transducers 16 constituting the transducer array transmit ultrasonic waves. Ultrasonic echoes reflected in the subject are sequentially received by the respective transducers 16 and each transducer 16 having received the ultrasonic echo outputs a reception signal to the corresponding reception signal processor 3. Then, the reception signal processors 3 process the reception signals sent through the channels of the transducers 16 to produce pieces of reception data, and the produced pieces of reception data are sequentially stored in the reception data memory 4.

Figure 3:
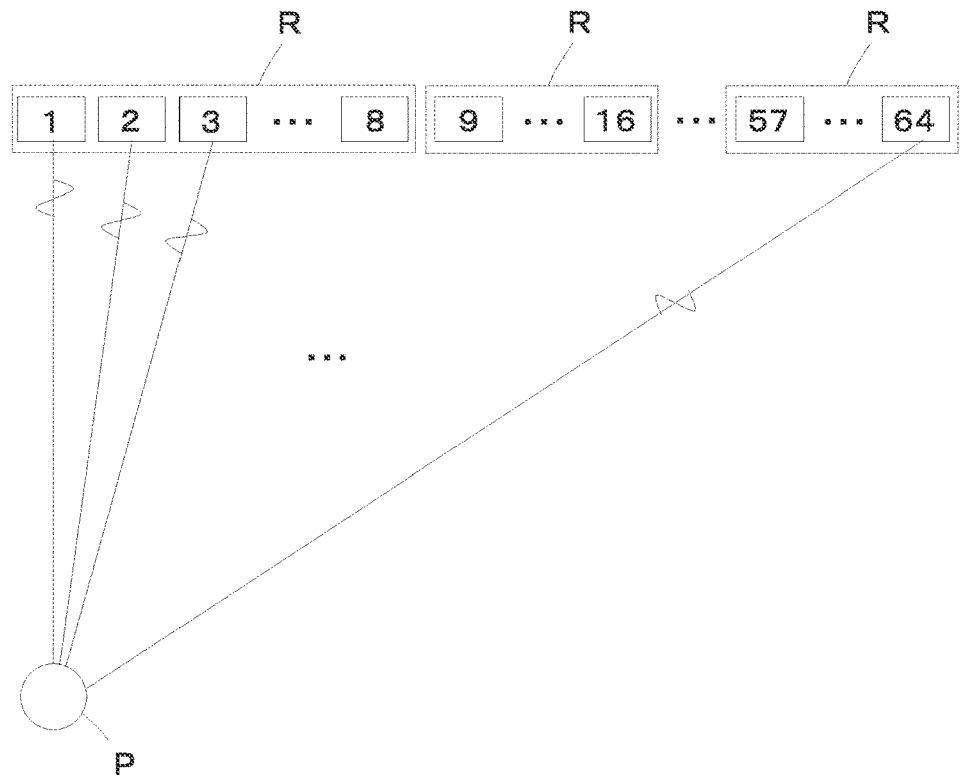
FIG. 3 is a diagram illustrating the reception of ultrasonic echo by each channel.

Specifically, in the case where, for instance, sixty-four transducers 16 are used to receive ultrasonic echoes, as shown in FIG. 3, ultrasonic echoes reflected at the reflection point P in the subject are received by the respective transducers 16 with time differences, and pieces of reception data which are acquired from the resulting reception signals, which are corresponding to the sixty-four channels and which have time differences are subjected to phasing addition, thereby producing one sound ray signal. Accordingly, given that, for example, the transmission and reception of ultrasonic waves are performed with a linear probe having sixty-four channels and a sampling frequency of 40 MHz and that reception signals are processed by 12-bit reception signal processors 3, reception data is produced, per unit time, in an amount of: 40 (MHz)×12 (bit)×64 (channels) =3.84 Gbyte/sec, in order to produce one sound ray signal. Assuming that the depth of scanning is about 4 cm here, the amount of reception data necessary for producing one sound ray signal is about 200 Kbytes.

While the amount of reception data is about 200 Kbytes, the capacity of a cache memory (primary cache) generally used is about several tens of kilobytes. Hence, when reception data acquired through all the channels are subjected to phasing addition in the phasing adder 19 at a time as in the case of hardware processing (including the case of Field-Programmable Gate Array (FPGA), the necessity arises for the calculation to repeatedly input and output the same reception data to and from the cache memory 18 and this causes frequent occurrence of cache-out.

To cope with it, according to the imaging conditions, the DBF controller 20 calculates in advance, as the total amount of reception data, the amount of reception data (reception data corresponding to sixty-four channels) necessary for the phasing adder 19 to produce one sound ray signal, divides the reception data stored in the reception data memory 4 into a plurality of groups based on the obtained total amount of reception data being about 200 Kbytes and the capacity of the DBF cache memory 18 being several tens of kilobytes, and controls the reception data IF unit 17 to transfer the groups of reception data from the reception data memory 4 to the DBF cache memory 18.

At that time, the DBF controller 20 divides the total amount of reception data corresponding to sixty-four channels of about 200 Kbytes into substantially equal sized groups in units of channels R so as to each fit into the capacity of the DBF cache memory 18, and transfers the reception data. For instance, the reception data corresponding to sixty-four channels are divided by eight and thus-obtained groups of reception data R each corresponding to eight channels are sequentially transferred to the DBF cache memory 18. The amount of one group of reception data R corresponding to eight channels is about 25 Kbytes and hence, can be adequately stored in the DBF cache memory 18 whose capacity is several tens of kilobytes. Preferably, the reception data to be transferred to the DBF cache memory 18 is divided into a plurality of groups so that each of the groups of reception data has the maximum size within the range capable of fitting into the capacity of the DBF cache memory 18. Owing to this configuration, the right amounts of groups of reception data can be sequentially transferred from the reception data memory 4 to the DBF cache memory 18.

The group of reception data corresponding to eight channels thus transferred to the DBF cache memory 18 is subjected to phasing addition in the phasing adder 19 under the control of the DBF controller 20, whereby a piece of phasing addition data is produced. Similarly, the phasing adder 19 performs phasing addition on the other groups of reception data each corresponding to eight channels and having been sequentially transferred to the DBF cache memory 18 by the reception data IF unit 17 so as to sequentially produce pieces of phasing addition data.

Thus, by dividing the reception data to be transferred from the reception data memory 4 to the DBF cache memory 18 into a plurality of groups in units of channels R, the phasing addition performed by the phasing adder 19 can be completed separately for each group of reception data. Specifically, the use of a group of reception data corresponding to eight channels and having been subjected to phasing addition is not required in phasing addition of another group of reception data corresponding to different eight channels. This configuration can reduce the number of times the same reception data is repeatedly input and output to and from the DBF cache memory 18 and accordingly, suppress the frequency of cache-out occurrence.

As described above, all the reception data corresponding to sixty-four channels are stepwise subjected to phasing addition to produce eight pieces of phasing addition data, which in turn are subjected to phasing addition by the phasing adder 19, thus performing beam forming to produce one sound ray signal.

The produced sound ray signal is transferred to the reception data memory 4 via the DBF cache memory 18 by the phasing adder 19 and the reception data IF unit 17 that are controlled by the DBF controller 20. At that time, the data amount of the sound ray signal is greatly compressed relative to the capacity of the DBF cache memory 18 and therefore the sound ray signal can be transferred to the reception data memory 4 without consuming the DBF cache memory 18.

As described above, sound ray signals thus produced by the phasing adder 19 are sequentially transferred to the reception data memory 4. Then, the signal processor 5 of the image producer 12 inputs the sound ray signals stored in the reception data memory 4 in units of frames to produce a B-mode image signal. The produced B-mode image signal undergoes raster conversion by the DSC 6 as well as gradation processing and the like by the image processor 7, and thereafter, based on this B-mode image signal, the display controller 8 displays an ultrasound diagnostic image on the display unit 9.

According to this embodiment, the total amount of reception data is obtained in advance based on the imaging conditions, the reception data is divided into a plurality of groups, and the groups of reception data are sequentially transferred to the DBF cache memory 18. This configuration can reduce the number of times the same reception data is repeatedly input and output to and from the DBF cache memory 18 and accordingly, suppress the frequency of cache-out occurrence. As a result, even when the digital beam forming processing is performed by a software, the excessive use of memory bandwidth can be avoided and the reception data acquired through each channel can be smoothly processed.

It should be noted that, in the foregoing embodiment, the linear probe having a sampling frequency of 40 MHz is used to transmit and receive ultrasonic waves, and reception data (about 200 Kbytes) for producing one sound ray signal is divided into equal sized groups of reception data each corresponding to eight channels (about 25 Kbytes for each) and then transferred to the DBF cache memory 18 (about 30 Kbytes), but the amount of data to be transferred may be changed depending on the total amount of reception data and the capacity of the DBF cache memory 18.

For example, given that the transmission and reception of ultrasonic waves are performed with a convex probe having sixty-four channels and a sampling frequency of 20 MHz and that reception signals are processed by 12-bit reception signal processors 3, reception data is produced, per unit time, in an amount of: 20 (MHz)×12 (bit)×64 (channels) =1.92 Gbyte/sec. Assuming that the depth of scanning is about 4 cm as in the foregoing embodiment, the amount of reception data necessary for producing one sound ray signal is about 100 Kbytes. Accordingly, the amount of reception data corresponding to thirty-two channels is about 50 Kbytes and hence, can be adequately stored in the DBF cache memory 18. The phasing adder 19 is therefore to perform phasing addition on every group of reception data corresponding to thirty-two channels.

Thus, since the amount of reception data used in the digital beam forming processing greatly varies depending on the imaging conditions, in order to transfer the right amount of reception data to the DBF cache memory 18, the amount of reception data to be transferred needs to be set after the total amount of reception data is calculated in advance based on the imaging conditions.

It should also be noted that, in the foregoing embodiment, the reception data is divided into a plurality of groups in units of channels and transferred to the DBF cache memory 18 but this invention is not limited thereto as long as the reception data is transferred so that the phasing addition performed by the phasing adder 19 is completed separately for each group of reception data. For instance, the reception data may be divided in the depth direction into a plurality of groups and transferred to the DBF cache memory 18 so that phasing addition is completed separately for each group of reception data.

It should also be noted that, in the foregoing embodiment, although a sound ray signal produced by the phasing adder 19 is transferred to the reception data memory 4 every time it is produced, the invention is not limited thereto as long as sound ray signals are transferred from the phasing adder 19 to the signal processor 4. For example, after a plurality of sound ray signals corresponding to one frame are produced by the phasing adder 19, the plurality of sound ray signals may be transferred to the reception data memory 4.

What is claimed is:

1. An ultrasound diagnostic apparatus comprising:
a transducer array having channels of a predetermined number;
a transmission driver configured to transmit ultrasonic beams from the transducer array toward a subject according to an imaging condition;
reception signal processors configured to process reception signals outputted through the channels of the transducer array having received ultrasonic echoes from the subject to acquire reception data;
a reception data memory unit configured to sequentially store therein reception data which have been acquired through the reception signal processors;
a beam forming unit having a cache memory;
a digital beam forming controller configured to:
divide the channels of the predetermined number into a plurality of channel groups;
divide the reception data stored in the reception data memory unit into a plurality of data groups that are substantially equal in size according to the imaging condition by a capacity of the cache memory so as to fit an amount of reception data in each of the plurality of data groups into the capacity of the cache memory, each of the plurality of data groups corresponding to a respective one of the plurality of channel groups thereby minimizing a frequency of cache-out occurrences; and
sequentially transfer divided reception data to the cache memory,
wherein the beam forming unit is configured to:
produce a plurality of subsets of phasing addition data based on the reception data of the plurality of data groups sequentially transferred to the cache memory by the digital beam forming controller; and
produce a plurality of sound ray signals, each of the plurality of sound ray signals being produced by subjecting the plurality of subsets of phasing addition data produced based on the reception data of the plurality of data groups to phasing addition; and
an image production unit configured to produce an ultrasound image from the plurality of sound ray signals produced by the beam forming unit.

2. The ultrasound diagnostic apparatus according to claim 1, wherein the digital beam forming controller controls the beam forming unit so as to sequentially perform the phasing addition on the reception data transferred from the reception data memory to the cache memory.

3. The ultrasound diagnostic apparatus according to claim 1, wherein the imaging condition is at least one of a frequency of ultrasonic waves, a scanning range and a scanning depth.

4. An ultrasound image producing method, comprising the steps of:
transmitting ultrasonic beams from a transducer array having channels of a predetermined number toward a subject according to an imaging condition;
producing reception data by processing reception signals, by reception signal processors, outputted through the channels of the transducer array having received ultrasonic echoes from the subject;
sequentially storing in a reception data memory unit the reception data which have been produced by the reception signal processors from the reception signals received by the channels of the transducer array;

dividing the channels of the predetermined number into a plurality of channel groups;
dividing the reception data stored in the reception data memory unit and having time differences into a plurality of data groups that are substantially equal in size according to the imaging condition by a capacity of a cache memory of a beam forming unit so as to fit an amount of reception data in each of the plurality of data groups into the capacity of the cache memory, each of the plurality of data groups corresponding to a respective one of the plurality of channel groups thereby minimizing a frequency of cache-out occurrences;
sequentially transferring divided reception data to the cache memory;
producing a plurality of subsets of phasing addition data based on the reception data of the plurality of data groups sequentially transferred to the cache memory;
producing a plurality of sound ray signals, each of the plurality of sound ray signals being produced by subjecting the plurality of subsets of phasing addition data produced based on the reception data of the plurality of data groups to phasing addition; and
producing an ultrasound image by an image production unit from the plurality of sound ray signals acquired through the beam forming unit.

5. An ultrasound diagnostic apparatus comprising:
a transducer array having channels of a predetermined number;
a transmission driver configured to transmit ultrasonic beams from the transducer array toward a subject according to an imaging condition;
reception signal processors configured to process reception signals outputted through the channels of the transducer array having received ultrasonic echoes from the subject to acquire reception data;
a reception data memory unit configured to sequentially store therein reception data which have been acquired through the reception signal processors;
a beam forming unit having a cache memory;
a digital beam forming controller configured to:
 divide in a depth direction the reception data stored in the reception data memory unit into a plurality of data groups that are substantially equal in size according to the imaging condition by a capacity of the cache memory so as to fit an amount of reception data in each of the plurality of data groups into the capacity of the cache memory thereby minimizing a frequency of cache-out occurrences; and
 sequentially transfer divided reception data to the cache memory,
wherein the beam forming unit is configured to:
produce a plurality of subsets of phasing addition data based on the reception data of the plurality of data groups sequentially transferred to the cache memory by the digital beam forming controller; and
produce a plurality of sound ray signals, each of the plurality of sound ray signals being produced by subjecting the plurality of subsets of phasing addition data produced based on the reception data of the plurality of data groups to phasing addition; and
an image production unit configured to produce an ultrasound image from the plurality of sound ray signals produced by the beam forming unit.

6. The ultrasound diagnostic apparatus according to claim 5, wherein the digital beam forming controller controls the beam forming unit so as to sequentially perform the phasing addition on the subsets of reception data transferred from the reception data memory to the cache memory.

7. The ultrasound diagnostic apparatus according to claim 5, wherein the imaging condition is at least one of a frequency of ultrasonic waves, a scanning range and a scanning depth.

8. An ultrasound image producing method, comprising the steps of:
transmitting ultrasonic beams from a transducer array having channels of a predetermined number toward a subject according to an imaging condition;
producing reception data by processing reception signals, by reception signal processors, outputted through the channels of the transducer array having received ultrasonic echoes from the subject;
sequentially storing in a reception data memory unit the reception data which have been produced by the reception signal processors from the reception signals received by the channels of the transducer array;
dividing in a depth direction the reception data stored in the reception data memory unit and having time differences into a plurality of data groups that are substantially equal in size according to the imaging condition by a capacity of a cache memory of a beam forming unit so as to fit an amount of reception data in each of the plurality of data groups into the capacity of the cache memory thereby minimizing a frequency of cache-out occurrences;
sequentially transferring divided reception data to the cache memory;
producing a plurality of subsets of phasing addition data based on the reception data of the plurality of data groups sequentially transferred to the cache memory;
producing a plurality of sound ray signals, each of the plurality of sound ray signals being produced by subjecting the plurality of subsets of phasing addition data produced based on the reception data of the plurality of data groups to phasing addition; and
producing an ultrasound image by an image production unit from the plurality of sound ray signals acquired through the beam forming unit.

* * * * *